United States Patent [19]

Kissin

[11] Patent Number: 4,585,002
[45] Date of Patent: Apr. 29, 1986

[54] METHOD AND APPARATUS FOR TREATMENT OF PAIN BY FREQUENTLY ALTERNATING TEMPERATURE STIMULATION

[76] Inventor: Igor Kissin, 1216 Ingram Ave., Birmingham, Ala. 35213

[21] Appl. No.: 725,950

[22] Filed: Apr. 22, 1985

[51] Int. Cl.$^4$ .............................................. A61B 10/00
[52] U.S. Cl. .................................................... 128/399
[58] Field of Search ........................................ 128/399

[56] References Cited

U.S. PATENT DOCUMENTS

| | | | |
|---|---|---|---|
| 3,168,895 | 2/1965 | Okuhara | 128/399 |
| 3,207,159 | 9/1965 | Tateisi | 128/399 |
| 3,533,397 | 10/1970 | Scher | 128/399 |
| 3,618,590 | 11/1971 | Frank | 128/2 R |
| 4,294,245 | 10/1981 | Bussey | 128/207.21 |

OTHER PUBLICATIONS

Elisabeth J. Fox, Ronald Melzack, "*Transcutaneous Electrical Stimulation and Acupuncture, Comparison of Treatment for Lower Back Pain*", Pain, 2 (1976) pp. 141–148.
R. Melzak et al, "*Ice Massage and Transcutaneous Electrical Stimulation Comparison of Treatment for Lower Back Pain*", Pain (9), 1980, pp. 209–217.
C. Norman Shealy, "*Six Years' Experience with Electrical Stimulation for Control of Pain*", Advances in Neurology, vol. 4, 1974.
Patrick D. Wall et al, "*Temporary Abolition of Pain in Man*", Science, 155: pp. 108–109, 1/6/67.
John M. Mennell, "*The Therapeutic Use of Cold*", Journal AOA/vol. 74, 8/75.
A Woodmansey et al, "*Vascular Reactions to the Contrast Bath in Health and in Rheumatoid Arthritis*", The Lancet, 2: pp. 1350–1353, 1938.

Primary Examiner—Richard C. Pinkham
Assistant Examiner—Leo P. Picard
Attorney, Agent, or Firm—Jennings, Carter, Thompson & Veal

[57] ABSTRACT

A method and apparatus for use in the treatment of pain through frequently alternating temperature stimulation uses a Peltier effect thermoelectric unit to induce thermal gradients in a patient's skin to selectively elevate and lower the temperature of the skin relative to a baseline skin temperature for brief intervals. The duration, intensity, frequency, and direction of the thermal gradient may be controlled via a microprocessor-based controller and a set of rheostats.

18 Claims, 2 Drawing Figures

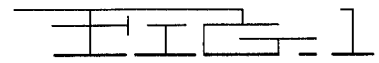
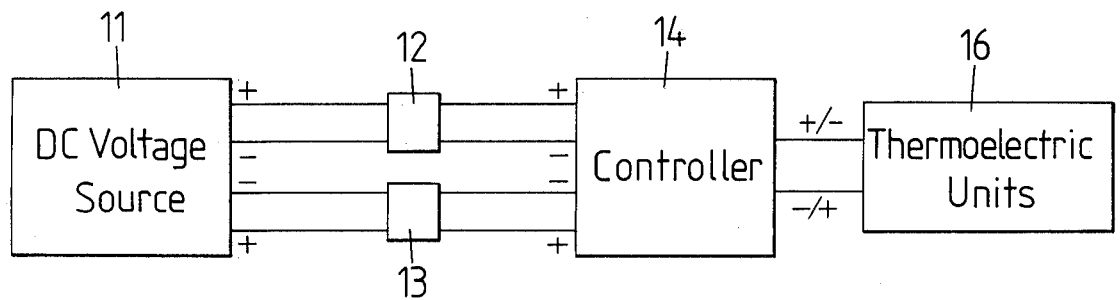
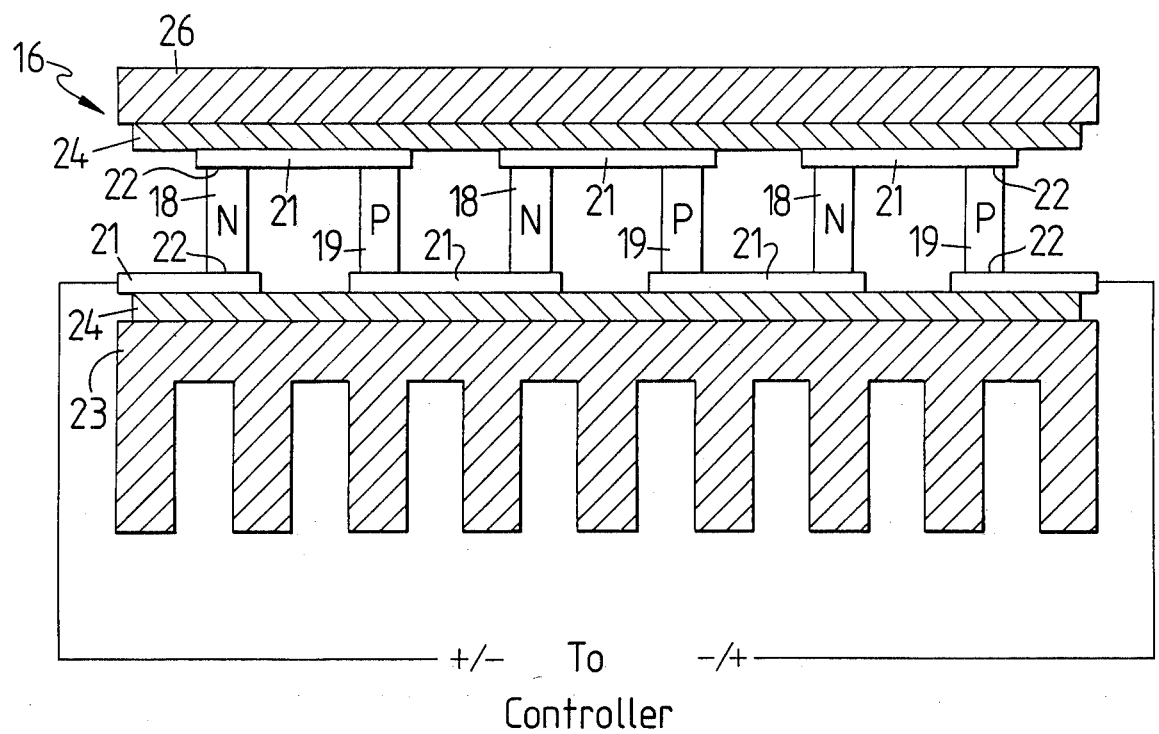
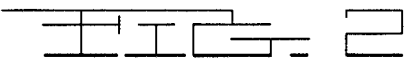

METHOD AND APPARATUS FOR TREATMENT OF PAIN BY FREQUENTLY ALTERNATING TEMPERATURE STIMULATION

FIELD OF THE INVENTION

The present invention relates to the field of medicine and more particularly to the relief of pain. Even more particularly the present invention relates to the field of somatosensory stimulation for the relief of pain. In even greater particularity, the present invention relates to thermal somatosensory stimulation and may be described as a method of treatment of pain in any localized area of the body through the application of frequently alternating temperature with the device used in the treatment.

BACKGROUND OF THE INVENTION

Various studies, dating back over at least the last fifty years, have indicated that somatosensory stimulation may provide pain relief. Thus, it is generally accepted that heat, cold, intense pressure or transcutaneous electric nerve stimulation (TENS) applied to the skin can decrease pain intensity. The TENS treatment involves a small electrical current passing through the skin stimulating sensory nerves.

Superficial local heat, such as hydro-collator pack and infrared heating, and theraputic cold such as ice and cold spray, are commonly used in muscoloskeletal, myofascial, arthritic, and other types of pain. Although not specifically used as a method of treatment for pain, the well known contrast bath method of alternate immersion of an extremity in large containers with hot and cold water every several minutes utilized the effect of temperature on peripheral vessels and general metabolism as a form of treatment for arthritic disorders. Studies have also shown that thermal skin stimulation with ice and TENS treatment are equally effective in treating low back pain, although thermal stimulation appears to be more effective for some pain patients. TENS, however, has the advantage over other conventional forms of somato-sensory stimulation because the TENS unit can be easily carried by the patient and, therefore, enables the patient to use it conveniently during typical daily activity. Unfortunately, several studies have shown that TENS treatment loses its effectiveness over time, apparently due to a habituation effect.

SUMMARY OF THE INVENTION

It is an object of the present invention to provide a non-invasive method and apparatus for treating pain through thermal somatosensory stimulation with frequently (several times per minute) changing applications of cold and heat which provides a new quality of sensory stimulation (through the introduction of dynamic temperature sensation).

Another object of the invention is to provide thermal somatosensory stimulation which is easily carried by the patient for use during typical daily activity.

Another object of the invention is to provide thermal somatosensory stimulation to any localized area of the body.

Another object of the invention is to provide thermal somatosensory stimulation which can be varied in amplitude, duration, and frequency of changes in direction (heat, cold).

Yet another object of the invention is to provide thermal somatosensory stimulation which can be conveniently interchanged with TENS treatment in an effort to decrease the habituation effect of either treatment used alone.

In order to advantageously accomplish these and other objects my invention utilizes a thermoelectric apparatus which is able to generate a thermal gradient within a predetermined temperature range, normally between 15° C. and 43° C. The thermoelectric apparatus generates a negative or positive thermal gradient dependent upon the direction of current flow through the apparatus. A controller is used to determine the direction of the current applied to the thermoelectric apparatus as well as the duration of the thermal gradient applied. The intensity of the temperature variation achieved is varied by controlling the amplitude of the direct electrical current applied to the thermoelectric device. Electrical power is preferentially supplied by a portable DC voltage source such as rechargeable batteries. The thermoelectric apparatus is adapted to be placed on the body adjacent the skin in an area associated with the pain. A physician or the patient under the physician's instructions may then adjust the intensity, frequency, and duration of each thermal gradient in a cycle to relieve the particular pain.

As a result of numerous investigations, the general physical correlates of intensity of warm and cold sensations, that is, the response of the thermoreceptors of the tissue, can be expressed as a function of the absolute temperature (T) of the skin and the rate of change (dT/dt) of skin temperature. The dynamic phase of the response of thermoreceptors is a function of temperature increment; the static phase of the response of thermoreceptors is a function of absolute temperature. Dynamic phase of the response of thermoreceptors is usually maximal within a five to fifteen second time interval after the start of change in temperature, then it begins to decline. The structure of temperature sensation is very complex; it is always difficult to determine when change in intensity of temperature sensation does in fact represent a combination of a change in intensity and in quality of sensation. I suggest that dynamic temperature sensation, the sensation of the change in temperature—dT/dt, is qualitatively different from static temperature sensation, the sensation of constant temperature. With cold stimulation, there is even electrophysiological evidence that thermoreceptors respond differently to dynamic and static phases of thermal stimulation, to wit: static phase exhibits bursts of impulses. My device provides pain relief with thermal stimulation that induces a dynamic phase of response in thermoreceptors. The dynamic phase gives a specific quality of somatosensory input.

DESCRIPTION OF THE DRAWINGS

Apparatus embodying features of my invention are depicted in the appended illustrations which form a part of this application, wherein:

FIG. 1 is a block diagram of my device for frequently alternating temperature stimulation; and, FIG. 2 is a sectional view of the thermoelectric unit.

DESCRIPTION OF A PREFERRED EMBODIMENT

Referring to FIG. 1, a portable DC power supply 11, such as D-size batteries, is connected to a pair of rheostats 12 and 13. Each rheostat controls a separate DC output from the power supply 11. The output of each rheostat is connected to a microprocessor based controller 14. An early prototype used a Cole-Parmer microprocessor-based controller which used AC for its power supply, however controllers operable from a DC supply are preferred. Controller 14 has a DC output to a thermoelectric unit 16, which may be one or more modules such as a module CP 1.4-71-06L by Material Electronic Products Corporation. A section illustration of a typical thermoelectric module suitable for the instant apparatus is shown in FIG. 2. The module operates due to the well known Peltier effect. In modules of this type, a plurality of thermoelectric cooling couples are made from two elements 18 and 19 of a semi-conductor, primarily Bismuth Telluride, heavily doped to create either an excess (N type) or deficiency (P-type) of electrons. The elements 18 and 19 are connected to an electric conductor 21 and thus form junctions 22 at each end of each element 18 or 19. When electrical current is applied one junction becomes cold while the other becomes hot. Heat absorbed at the cold junction is pumped to the hot junction at a rate proportional to carrier current passing through the circuit and the number of couples. Reversing the direction of the current reverses the thermal nature of the junction. The particular module noted hereinabove had 71 couples and measured 30×30 mm with a 3.8 mm width. The module is coated with an electrical insulator 24 such as metalized ceramic and has one side thereof bonded to an aluminum natural convection heat sink 23 made by Borg Warner Corporation. The other side of the unit 16 is applied to the patient's skin 26.

The thermoelectric unit 16 is used to create a thermal gradient with respect to a baseline skin temperature. The controller 14 is used to control the direction of the gradient by selecting the direction of current flow through the thermoelectric unit 16. The controller 14 also controls the duration of the gradient. The intensity or rate of change of the thermal gradient is determined by the setting of the associated rheostat 12 or 13. By varying the commands given by the controller and the settings of the rheostats, the direction, duration, frequency, and intensity of the thermal gradient may be customized for a specific treatment. Typically the duration of cooling or heating may vary independently from a length of five seconds to sixty seconds.

Since the device provides wide and independent control over the cooling and heating, three types of temperature stimulation may be provided:

Type I—Temperature fluctuations at the baseline level of skin temperature. Heating brings the skin temperature above the baseline level of the area to 40° to 43° C., and cooling decreases the skin temperature below the baseline level to 15° to 25° C.

Type II—Temperature fluctuation above the baseline level of skin temperature. Heating brings the skin temperature above the baseline level to 40° to 43° C., and cooling decreases the skin temperature, although not below the baseline level. Fluctuation of the skin temperature will thus be above the baseline level for the area to which the thermoelectric unit 16 is applied.

Type III—Temperature fluctuation below baseline level of skin temperature. Cooling brings the skin temperature below the baseline level to below 15° to 20° C., and heating increases the skin temperature, although not above the baseline level. Fluctuation of skin temperature will be below the usual level for the area to which the unit 16 is applied.

Experimentally, it appears that tension headache treatment is most effective when type III temperature stimulation is applied. In this instance, with occipital location of the headache, the thermoelectric units 16 are placed on the baseline between the neck and head, two centimeters to the right and left of a line going through the spinous processes. Temperature fluctuation within the 32° to 22° C. range produced fifty to eighty percent pain relief.

The most effective treatment for chronic low back pain was Type I stimulation. The thermoelectric units 16 were attached to the skin of the back of the $L_4$–$L_5$ level, four to five centimeters to the right and to the left from midline. Temperature fluctuation ranging from 42° C. to 25° C. relieved about fifty per cent of the pain.

The most important feature of the device is that it is designed to induce a dynamic phase of response in thermoreceptors. Therefore, the ability of my device to provide a change in direction of the thermal gradient as frequently as every five to thirty seconds (much more frequently than the contrast bath treatment) corresponds with the time interval when the dynamic phase of response of thermoreceptors gives its maximal somatosensory input and therefore it gives a new dimension of sensory stimulation as compared to the prior art.

It is to be understood that the thermoelectric module 16 can be adapted for treatment of virtually any region of the body, and the remaining components can be small enough to permit the patient to carry the device about and use the device without significant interference during normal daily activity. Also, the temperature ranges cited hereinabove are exemplary rather than limitations. Furthermore, adaptation, which is a typical feature that decreases the sensory effect of constant temperature stimulation, can be avoided to a very significant extent with this method and apparatus.

While I have shown my invention in but one form, it will be obvious to those skilled in the art that it is not so limited, but is susceptible of various changes and modifications without departing from the spirit thereof.

What I claim is:

1. Apparatus for treatment of pain by iterative application of a thermal gradient to the skin comprising:
   (a) thermoelectric means for generating a thermal gradient in adjacent skin tissue responsive to an electrical current input thereto;
   (b) controller means operatively connected to said thermoelectric means for adjusting the duration of the application of said thermal gradient and the direction of the thermal gradient periodically whereby the direction of said thermal gradient is reversed at least once per minute; and
   (c) means for varying the intensity of said thermal gradient by varying amplitude of the electrical current input to said thermoelectric means.

2. Apparatus as defined in claim 1 wherein said thermoelectric means comprises:
   (a) a thermally conductive plate adapted for contact on one side thereof with the skin on a predetermined area of the body;
   (b) a plurality of thermally responsive semi-conductors operably connected to one side of said plate for inducing a thermal gradient therein in accordance with the amplitude and direction of electrical current flow through said semi-conductors;
   (c) a heat sink operably connected to said semi-conductors for dissipating excess heat therefrom; and (d) a second thermally conductive plate intermediate said semi-conductors and said heat sink.

3. Apparatus as defined in claim 2 wherein said means for varying the intensity of said thermal gradient comprises:
   (a) a negative gradient rheostat operably connected to said controller means for varying the electrical current thereto when said thermal gradient has a negative slope; and
   (b) a positive gradient rheostat operably connected to said controller means for varying the electrical current thereto when said thermal gradient has a positive slope.

4. Apparatus as defined in claim 2 wherein said controller means comprises:
   (a) means for selecting the direction of current flow through said semi-conductors; and
   (b) means for varying the diration of current flow in a selected direction.

5. Apparatus as defined in claim 4 wherein the duration of current flow in a selected direction is variable within a duration range of five seconds to sixty seconds.

6. Apparatus as defined in claim 4 wherein the skin temperature is varied by said plate between a lower temperature of 15° C. and an upper temperature of 43° C.

7. Apparatus defined in claim 1 wherein said controller means comprises means for selecting the direction of current flow through said thermoelectric means; and means for varying the duration of current flow in a selected direction.

8. Apparatus as defined in claim 7 wherein the duration of current flow is variable within a duration range of five seconds to sixty seconds.

9. Apparatus as defined in claim 7 wherein the thermoelectric means varies the skin temperature between a lower temperature of 15° C. and an upper temperature of 43° C.

10. Apparatus as defined in claim 1 further comprising a portable power supply operably connected to provide electrical current to said thermoelectric means.

11. Apparatus for treatment of pain by iterative application of a thermal gradient to the skin, comprising:
   (a) thermoelectric means for generating a thermal gradient proximal the skin responsive to an electrical current input thereto; and
   (b) controller means operably connected to said thermoelectric means for controlling the duration and intensity of said thermal gradient and reversing the direction of said thermal gradient at least once per minute.

12. A method for treatment of pain comprising the steps of:
   (a) applying a thermal gradient to the skin by placing a thermoelectric apparatus adjacent the skin over a local area associated with the pain whereby the temperature of the skin is varied within a predetermined range relative to predetermined baseline temperature;
   (b) varying the duration of said thermal gradient within a predetermined range; and
   (c) varying the direction of said thermal gradient at least once per minute.

13. The method of claim 12 wherein said applying step comprises:
   (a) varying the temperature of said thermoelectric apparatus by introducing electrical current flow therethrough, and
   (b) controlling the intensity of said temperature variation by controlling the amplitude of electrical current passing through said thermoelectric apparatus.

14. The method of claim 13 wherein the direction of said thermal gradient is varied by varying the direction of current flow through said thermoelectric apparatus.

15. The method of claim 12 wherein the duration of said thermal gradient lasts between five and sixty seconds.

16. The method of claim 12 wherein the said predetermined range is from 15° C. to 43° C.

17. The method of claim 12 wherein the predetermined range is between said baseline temperature and 43° C.

18. The method of claim 12 wherein said predetermined range is between said baseline temperature and 15° C.

* * * * *